(12) United States Patent
Lambert (10) Patent No.: US 6,952,912 B2
(45) Date of Patent: *Oct. 11, 2005

(54) METHOD AND DEVICE FOR ANALYZING RESPIRATORY SOUNDS IN HORSES

(75) Inventor: David H. Lambert, Lexington, KY (US)

(73) Assignee: Airway Dynamics, LLC, Midway, KY (US)

( * ) Notice: Subject to any disclaimer, the term of this patent is extended or adjusted under 35 U.S.C. 154(b) by 67 days.

This patent is subject to a terminal disclaimer.

(21) Appl. No.: 10/368,802

(22) Filed: Feb. 19, 2003

(65) Prior Publication Data

US 2003/0212348 A1 Nov. 13, 2003

Related U.S. Application Data

(63) Continuation-in-part of application No. 09/927,806, filed on Aug. 10, 2001, now Pat. No. 6,602,209.
(60) Provisional application No. 60/224,490, filed on Aug. 11, 2000, and provisional application No. 60/357,769, filed on Feb. 19, 2002.

(51) Int. Cl.[7] .............................. A61B 5/08; B68B 1/04; B68B 1/00
(52) U.S. Cl. ................................. 54/6.1; 54/1; 600/529
(58) Field of Search ........................... 54/1, 6.1, 11, 10, 54/12, 80.1, 80.2, 71; 600/529

(56) References Cited

U.S. PATENT DOCUMENTS

| | | | |
|---|---|---|---|
| 1,057,529 A | * | 4/1913 | Cloninger ........................ 54/1 |
| 3,990,435 A | | 11/1976 | Murphy |
| 4,218,584 A | | 8/1980 | Attenburrow |
| 4,261,293 A | * | 4/1981 | Djernes ........................ 54/11 |
| 4,720,866 A | | 1/1988 | Elias et al. |
| 4,774,679 A | | 9/1988 | Carlin ........................ 702/41 |
| 4,955,372 A | | 9/1990 | Blackmer et al. ...... 128/203.16 |
| 5,165,417 A | | 11/1992 | Murphy, Jr. |
| 5,503,141 A | | 4/1996 | Kettl et al. |
| 5,566,645 A | * | 10/1996 | Cole ............................. 54/71 |
| 5,737,280 A | | 4/1998 | Kokubo ........................ 368/2 |
| 5,737,429 A | | 4/1998 | Lee |
| 5,782,240 A | | 7/1998 | Raviv et al. ................ 600/484 |
| 5,853,005 A | | 12/1998 | Scanlon |

(Continued)

OTHER PUBLICATIONS

Attenburrow, D.P.;"Respiratory Sounds Recorded by Radio–Stethoscope from Normal Horses at Exercise"; Equine Veterninary Journal (1978), 10 (3), pp. 176–179.

(Continued)

*Primary Examiner*—Teri Pham Luu
*Assistant Examiner*—Elizabeth Shaw (57) ABSTRACT

The invention provides a device and a method for recording respiratory sounds in exercising horses thereby enabling the user identify upper airway abnormalities and/or evaluate athletic potential by, e.g., measuring expiratory and/or inspiratory times during exercise under field and/or actual racing conditions. In particular, the invention provides a respiratory monitoring system or device in which a transducer or microphone is placed in direct contact with the skin of the subject animal overlying the skull, e.g., the frontal sinus or nasal turbinates and thereby enable recording and analysis of upper airway respiratory sound from the exercising animal. In one embodiment, the invention provides a device wherein the transducer or microphone is positioned or embedded within a gel pad or other suitable medium and the device placed in direct contact with the skin of the animal overlying, e.g., the skull, sinus or nasal turbinates of the horse The device of the invention provides an acoustic monitoring system capable of direct attachment to the head of a racing horse which produces an output signal that is not diluted, attenuated or otherwise corrupted by noises such as wind, hoof beats and/or treadmill noises.

17 Claims, 4 Drawing Sheets

U.S. PATENT DOCUMENTS

| | | |
|---|---|---|
| 6,168,568 B1 | 1/2001 | Gavriely ..................... 600/529 |
| 6,228,037 B1 | 5/2001 | Derksen ..................... 600/529 |
| 6,287,264 B1 | 9/2001 | Hoffman |
| 6,602,209 B2 * | 8/2003 | Lambert et al. ............ 600/529 |
| 2002/0156391 A1 | 10/2002 | Derksen et al. |

OTHER PUBLICATIONS

Belknap, James K., et al;"Failure of Subtotal Arytenoidectomy to Improve Upper Airway Flow Mechanics In Exercising Standardbreds with Induced Laryngeal Hemiplegia"; Am J Vet Res. vol. 51 No. 9, Sep. 1990, pp. 1481–1487.

Barnes, G.R.G.,et al; "Sound Spectography in the Diagnosis of Equine Respiratory Disorders: a Preliminary Report"; New Zealand Veterinary Journal (1979) vol. 27, pp. 145–146.

Attenburrow, D.P.; "Time Relationship Between the Respiratory Cycle and Limb Cycle in the Horse"; Equine Veterinary Journal; (1982) 14 (1), pp. 69–72.

Hornickle, H., et al; "Respiration in Exercising Horses"; Equine Exercise Physiology, (1987), pp. 7–16.

Attenburrow, D.P.; "Respiration and Locomotion"; Equine Exercise Physiology (1984) pp. 17–22.

Lafortuna, CL. et al; "The Effects of Locomotor–Respiratory Coupling on the Pattern of Breathing in Horses"; J. Physiology,(1996) Apr. 15; 492(Pt2); 587–96 (Abstract).

Hobo, S, et al "Characteristics of Respiratory Function During Swimming Excercise in Thoroughbreds"; J. Vet. Med. Science (1998) Jun., 60 (6): 687–9 (Abstract).

Art, T., et al; "Pulmonary Mechanics during Treadmill Exerise in Race Ponies"; Vet. Res. Common (1988); 12(2–3): 245–58 (Abstract).

Subburaj, S., et al; "Methods of Recording and Analysing Cough Sounds"; Pulmonary Pharmacology (1996) 9, pp. 269–279.

King, Marcia; "Upper Airway Problems"; The Horse; Jul. 2003; pp. 53–58.

Derksen, Frederik J. et al, "Spectrogram Analysis of Respiratory Sounds in Exercising Horses" AAEP Proceedings, (1999), vol. 45, pp. 314–315.

Attenburrow, D.P., "The Development of a Radio–Stethoscope for use in the Horse at Rest and during Exercise", Equine Veterinary Journal, (1978), 10, (1), pp. 14–17.

Seeherman, "Current Therapy in Equine Medicine", (1997), pp 404–407.

Ducharme et al, "Current Therapy in Equine Medicine", (1997), pp 415–418.

Attenburrow, D.P., "Resonant Frequency of the Lateral Ventrical and Saccule and Whistling", Equine Exercise Physiology, pp 27–32.

Lindell, C., "Limited Geographic Variation in the Vocalizations of a Neotropical Fumariid, *Synallaxis Albescens*", Wilson Bull., 110(3), 1998, pp. 368–374.

Parente, E.J. et al, "Upper Respiratory Dysfunctions in Horses During High–Speed Exercise", AAEP $40^{th}$ Annual Convention Proceedings, 1994, pp 81–82.

Perez–Padilla, Jr et al. "Characteristics of the snoring noise in patients with and without occlusive sleep apnea", Am Rev Respir Dis. Mar. 1993: 147(3):635–44.

Fletcher, S et al; "Onboard acoustic recording from diving northern elephant seals", J Acoust Soc Am. Oct. 1996; 100 (4 PI):2531–9.

Pasterkamp, H. et al; "Measurement of respiratory acoustical signals. Comparison of sensors", Chest. Nov. 1993; 104(5); 1518–25.

* cited by examiner

METHOD AND DEVICE FOR ANALYZING RESPIRATORY SOUNDS IN HORSES

This application is a continuation in part of U.S. patent application Ser. No. 09/927,806 filed Aug. 10, 2001 now U.S. Pat. No. 6,602,209 which claims the benefit of priority in U.S. Provisional Application Ser. No.: 60/224,490, filed on Aug. 11, 2000 and U.S. Provisional Application Ser. No. 60/357,769 filed on Feb. 19, 2002.

FIELD OF THE INVENTION

The present invention relates generally to the performance and athletic potential of horses. In particular, the present invention relates to an improved device and method for analysis of respiratory sounds produced by an exercising horse. The present invention also relates to an improved device and method to diagnose upper airway pathology in exercising horses, especially racing horses. Most particularly, the present invention relates to an improved device and method of diagnosing a pathological upper airway condition and/or to a method of predicting racing performance by analysis of recorded respiratory sound in galloping or racing thoroughbred racehorses.

BACKGROUND OF THE INVENTION

In the late 1970's D. P. Attenburrow et al. developed a device for recording sound over the trachea which included a radiostethoscope and a spectrogram analysis of inspiratory and expiratory sounds of horses at rest and during exercise (See, e.g., Attenburrow, D. P., "The Development of a Radio-Stethoscope for use in the Horse at Rest and During Exercise", *Equine Vet J.* (1978), 10, (1), 14–17; Attenburrow, D. P., "Respiratory Sounds Recorded From Normal Horses at Exercise" *Equine Vet J.* (1978), 10, (3), 176–179; and U.S. Pat. No. 4,218,584 to Attenburrow). Later, however, it was found that sounds recorded over the trachea do not necessarily directly relate to the functionally significant respiratory sounds of the exercising horse, see, e.g., Derksen et al. "Spectrogram Analysis of Respiratory Sounds in Exercising Horses", AAEP Proceedings, Vol. 45, pp.314–15 (1999) (See also, U.S. Pat. No. 6,228,037 to Derksen.) and the U.S. Patent Publication No.: 2002/0156391 A1 to Derksen et al.

In the '037 patent, Derksen et al. advocate the use of a large and cumbersome microphone positioned in front of the horses nostrils and a recording device which can be placed alongside a horse exercising on a treadmill to pick up normal as well as abnormal respiratory sounds and assess pathology of the upper airway based upon the sound patterns produced during exercise, e.g., for detection of laryngeal hemiplegia and dorsal displacement of the soft palate. Derksen's analytical systems, however, are limited in that they are difficult to use on a galloping horse under field conditions, e.g., on a horse with a rider (e.g., breezing or working) on a training track and cannot be used during an actual race or competition event. In addition, the Derksen device, by design, picks up respiratory sounds at close proximity to the nostrils of the horse which, in the galloping horse, can also include extraneous and unwanted sounds, e.g., percussion noise of the hoofs contacting the training surface and wind noise.

As with the Derksen device, the Attenburrow et al. radiostethoscope may be limited in that it cannot conveniently be used under field or actual racing conditions and, moreover, may not be capable of detection of subtle changes in upper airway respiratory sound induced by subclinical pathological change. Thus, there still exists a need in the art for a device and method which enables analysis of such parameters in the equine athlete under field and/or racing conditions.

Once an individual race horse prospect has been selected by its owner and the training and racing process begins, some individual horses will not perform up to their "estimated" or "anticipated" potential. Oftentimes, subtle pathological changes or even slight developmental abnormalities (which may be subclinical or non-apparent to the naked eye) are present in the subject horse's upper airway and can be responsible, at least in part, for the animal's sub-par performance at a particular racing level. Thus, there exists a need in the art for a device suitable for detection of these subtle pathological changes in the upper airway which can be attached directly to the horse and thereby enable recording and analysis of respiratory sounds generated at racing speeds, e.g., during an actual race.

U.S. Pat. No. : 5,853,005 to Scanlon discloses a sound and movement monitor comprised of a transducer with a fluid filled pad held in close contact against a sound or movement source for monitoring acoustic signals transferred into the fluid. The use of a fluid filled medium and transducer, however, presents problems with vibrational movement, e.g., hoof beat percussion from the intensely exercising animal. Thus, there still exists a need in the art for a device which can be attached directly to the horse which enables accurate detection of and analysis of respiratory sounds in the equine athlete exercising under field conditions that does not suffer from these shortcomings.

OBJECTS OF THE INVENTION

It is an object of this invention to provide an improved device and method for facilitating the recording of respiratory sounds in exercising horses.

It is a further object of the invention to provide a method for recording respiratory sounds in exercising horses to identify upper airway abnormalities and/or evaluate athletic potential by, e.g., measuring expiratory and/or inspiratory times during exercise.

A more specific objective of the present invention is to provide a respiratory monitoring system in which a transducer or microphone may be placed in direct contact with the skin of the animal overlying the skull, sinus or nasal turbinate and thereby enable recording and analysis of upper airway respiratory sound from the exercising animal.

An additional object of the invention is to provide a device wherein the transducer or microphone is positioned or embedded within a gel pad or other suitable medium and the device placed in direct contact with the skin of the animal overlying, e.g., the skull, sinus or nasal turbinates of the horse.

It is another object of this invention to provide a device and monitoring system having multiple transducers for providing a more accurate reading of upper respiratory sounds and thereby a means to identify the presence of and locality of an upper respiratory abnormality.

It is also an object of the present invention to provide an acoustic monitoring system which produces an output signal that is not diluted, attenuated or otherwise corrupted by noises such as wind, hoof beats and or treadmill noises.

It is also an object of the present invention to provide an acoustic monitoring system comprised of a device capable of direct attachment to the head of a racing horse which produces an output signal that is not diluted, attenuated or otherwise corrupted by noises such as wind, hoof beats and/or treadmill noises.

Yet another object of the invention is to provide a method for relating the respiratory constraints of an individual horse as a predictor of athletic performance of the horse.

Still another object of this invention is to provide a device and a method for analysis of respiratory sounds that can be used while the horse is being exercised under natural conditions e.g. galloping on a training track or field.

SUMMARY OF THE INVENTION

The present invention provides a device and a method for recording respiratory sounds in exercising horses thereby enabling the user identify upper airway abnormalities and/or evaluate athletic potential by, e.g., measuring expiratory and/or inspiratory times during exercise.

In particular, the present invention provides a respiratory monitoring system or device in which a transducer or microphone is placed in direct contact with the skin of the subject animal overlying the skull, sinus or nasal turbinate and thereby enable recording and analysis of upper airway respiratory sound from the exercising animal. In one embodiment, the invention provides a device wherein the transducer or microphone is positioned or embedded within a gel pad or other suitable medium and the device placed in direct contact with the skin of the animal overlying, e.g., the skull, sinus or nasal turbinates of the horse The device of the invention provides an acoustic monitoring system capable of direct attachment to the head of a racing horse which produces an output signal that is not diluted, attenuated or otherwise corrupted by noises such as wind, hoof beats and/or treadmill noises.

DETAILED DESCRIPTION OF THE INVENTION

Throughout the application, various references and patents are cited, the contents of which are hereby incorporated herein by reference.

Additional objects, advantages and other novel features of the invention will be set forth in part in the description that follows and in part will become apparent to those skilled in the art upon examination of the foregoing or may be learned with the practice of the invention.

When a horse gallops or runs, it normally breaths in a rhythm of inhalation and exhalation which is in relation to the horse's stride. The normal galloping horse will usually take one breath with each full stride, exhaling or breathing out only when its front legs are in contact with the ground. The force generated when the front legs strike the ground aids in compressing the upper abdomen and thereby assisting in evacuating (expiring or exhaling) air from the lungs.

Upper airway obstructions are common and often associated with abnormal respiratory noise and/or decreased athletic performance in the horse/animal. Respiratory sounds in horses that are exercising are difficult to evaluate because respiratory sounds can be obscured by noises such as hoof beats, wind noise or sounds from equipment such as a treadmill on which the horse is exercising. Moreover, if the upper airway pathology is "subclinical" (not discernable to the naked eye, e.g., during an endoscopic examination of the upper airway), the abnormal respiratory sounds produced may likewise be non-discernable to the unaided ear.

In addition, it has been found that the placement of the microphone influences the sound recordings obtained of the respiration in the animal. Prior to the instant invention, there has been no system that accurately, economically and conveniently monitors respiratory sounds, e.g., sounds produced from an upper airway obstruction in horses exercising under field or actual racing conditions.

Set forth in greater detail below are specific details related to an improved device and method for recording, monitoring and/or analyzing respiratory sounds in exercising horses and for predicting athletic performance in such an animal. The examples set forth herein are in no way intended to limit the scope of the invention. Those of skill in the art will realize that, given the teachings provided herein, many variations of the methods are possible that will fall within the scope of the general concept that it is now possible to predict athletic potential by analysis of respiratory sounds and identification of upper airway abnormalities and/or functional limitations of a subject equine's upper airway.

Thus, the present invention provides a device and a method for recording and analyzing upper airway sounds generated during exercise and for identification of abnormalities or pathological change in an animal, e.g., a dog or a horse. The present invention also provides a device and a method for recording and analyzing upper airway sounds generated during exercise and for measuring expiratory and/or inspiratory times during exercise and relating such information to analyze the animal's upper respiratory sounds and potential to athletically excel. While the methods and general concepts disclosed herein are particularly useful for predicting athletic performance in horses, one of ordinary skill in the art can appreciate that the methods set forth herein can be utilized to predict athletic performance on any animal including, but not limited to horses or dogs.

One presently preferred embodiment discloses a method for predicting the athletic performance of a horse by determining the condition and/or functional limitations of the upper airway, e.g., function of the larynx, pharynx, arytenoid cartilages, epiglottis and/or the airflow limitations of the upper airway. This can be accomplished in a variety of ways, but is most accurately done by actually measuring the respiratory sounds of the upper airway of the horse using one or more transducers (e.g., microphones) that are directly applied to the surface of the skin overlying e.g., the frontal sinuses or the skull (e.g., the forehead) of the horse.

Briefly, one embodiment of the invention provides a method for determining upper respiratory abnormalities of the exercising animal under field conditions comprising: placing a device comprised of one or more specially adapted microphone(s) on the subject horse at a predetermined location thereon for registering the sounds of breathing (inspiration and expiration) during exercise under field conditions; exercising (galloping) the subject horse; recording the sounds of breathing produced thereby and analyzing the recorded sound. In one embodiment, the expiration and inspiration by the horse creates a generation of analog signals from the transducers that are conditioned and digitized by the signal processing circuitry and stored by the computer. These recorded sounds can then be analyzed using, e.g., spectrogram software as set forth in Derksen et al. or by other methods known in the art, e.g., via commercially available software which can display the recorded sounds graphically on a computer such that sounds of inspiration can be distinguished from expiration etc. In addition, the horse's speed (velocity) can be timed while the sound data is being recorded and relationships established between breathing times and upper respiratory abnormalities.

In a presently preferred embodiment of the invention, the method of diagnosing upper respiratory abnormalities by analysis of respiratory sounds and upper respiratory air flow in an animal comprises a sound transducer applied to the skin overlying the skull or adjacent to a sinus or over the nasal turbinates of the horse. The microphone may be directly applied or attached to the skin or preferably is encased in a suitable medium such as rubber, latex or a suitable gel pad consisting with the microphone embedded therein and adapted to conform to the skull of the horse or to be adapted to fit on the head of a horse in the embodiment of a hood (blinkers type apparatus) or an adaptation thereof. It is also contemplated that the microphone can be mounted to a caverson, a halter or halter-type apparatus or a bridle and the like.

Briefly, one preferred method of the invention comprises positioning a microphone at a desired location and in direct contact on the head of the horse which is capable of picking up sound emitted from the horse as he/she breathes during exercise. The microphone can be any of a variety of small portable microphones that are commercially available. For example, one presently preferred microphone is the ATR-35s Lavalier microphone manufactured by audio-technia® of Stow, Ohio. This particular microphone is omnidirectional with an available frequency range of about 50–18,000 Hz, sensitivity of about −54 dBm±3 dB, 1 kHz at 1 Pa, and with an impedance of 1000 ohms±30%. However, it is contemplated that a unidirectional microphone can also be utilized. The microphone may be directly attached to the skin of the subject animal but more preferably is embedded within a suitable material such as rubber, latex plasctic or the like as set forth more fully below. The microphone is then positioned on the head of the horse such that the embedding material is in direct contact with the skin of the horse at the desired location.

The microphone can be attached to a portable recording device, e.g., a portable (micro) cassette recorder or digital recorder, and the recorder is, in turn, mounted on the horse or the rider as desired. Examples of presently preferred recording devices include the Sony® standard VOR micro cassette recorder, Model M-950 with detachable speaker and the Sony® Digital "MD"(MiniDisc) Model MZ-R70 Walkman®. The mini disc, for example, has a frequency response from about 20 to about 20,000 Hz±3 dB. Alternatively, the recording signal from the microphone can be transmitted to the recording device via telemetry utilizing telemetric means known in the art.

One embodiment of the invention provides a device for attaching the recording device and microphone to the subject horse. In the presently preferred embodiment shown in FIG. 6, the device 100 is a lightweight hood or garment (similar to a traditional "blinkers" device commonly used in horse racing) which placed on the subject horses head (See, e.g., applicant's co-pending application published as International Publication Number WO 02/13938 A2). The device is made to fit snugly over the face (forehead and bridge of the nose) having a band of material extending from the bridge of the nose dorsally over the poll (just behind the ears) with holes cut out for the ears and eyes. The garment wraps around the face and head and is attached via e.g., a hook and loop type fastener (e.g., VELCRO™) at the throat latch. A first pouch or pocket is configured to contain the microphone such that the recording surface of the microphone is urged toward and held in direct contact with the horses skin at a desired location, e.g., against the skull of the horse on the midline (forehead), over the frontal sinus, or over the nasal turbinates and the like.

Figure 6:
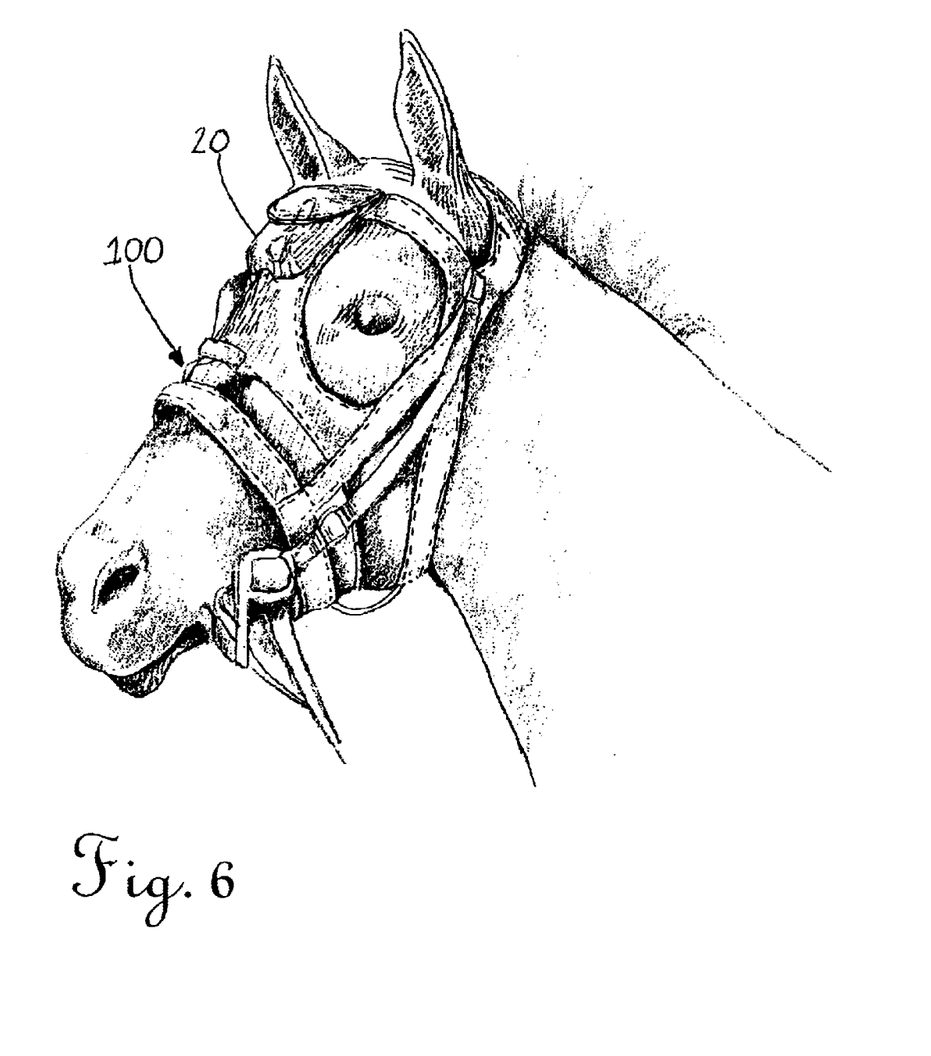
FIG. 6 is a perspective view of a lightweight hood of garment (similar to a traditional "blinkers" device commonly used in horse racing) which is placed on the subject horses head.

A second pouch or closeable pocket can be locate, e.g., on the front of the garment for removable placement of the recording device. It is presently desired that the pouch be located on the midline of the horse's forehead between and slightly anterior or dorsal to the horse's eyes so as not to interfere with the field of vision while the horse is exercising. Suitable materials for the hood or garment of the invention include, but are not limited to nylon, cloth or other suitable lightweight fabrics. Alternatively, a single pouch 20 can be utilized to house both the microphone and the portable recording device such as is shown in FIG. 6.

The hood, with the recording device and microphone attached, is placed on the subject horse's head and the horse is then asked to perform a desired exercise routine. Generally the horse is trotted or jogged a sufficient distance as a warm up before it is asked to gallop or breeze. A recording is made of the respiratory sounds emitted during the exercise event and preserved for analysis. Likewise, the subject animal's speed is recorded and, if desired, a video tape of the exercise event is made which can later be correlated with the sound recording and velocity in calculating stance time and/or stance distances, expiratory times (ET) and maximum comfortable velocity (MCV) e.g., as set forth in applicant's co-pending application published as International Publication Number WO 02/13938 A2.

Specially adapted computer software is utilized for analysis of the recording. In a presently preferred embodiment, "Spectrogram" software (available from R. S. Horne at, e.g., www.monumental.com/rshorne/gram.html) or the spectrogram software from available DolphinEAR, United Kingdom (e.g., at www.dolphinear.com) is utilized for the analysis. This program provides a visual graph of the recorded sound which plots frequency range against time. In this spectrogram program, digital audio recordings (.WAV format) can be analyzed to produce a plot of frequency versus time, with amplitude represented by a variable color scale and can be useful for revealing hidden or subclinical frequency structure of audio signals and for identification and classification of particular sounds emitted from the upper airway during the exercise event.

The typical display band of frequencies ranges from about zero Hz to about 6,000 Hz. Exhalation sounds generally have higher amplitude in the lower frequency ranges e.g., from less than about 2 kHz and especially less than about 1 kHz. Inspiratory sounds typically extend into the higher frequency ranges e.g., above about 2 kHz up to about 6 kHz. Using the presently preferred Spectrogram software, the recorded sound is analyzed and inspiratory and expiratory times are carefully measured and upper airway sounds are analyzed.

In another preferred embodiment the transducers or microphones of the invention can consist of consist of, for example, the Emkay BL 1785, Emkay WP Series Microphone, Emkay MR-BJ Series Microphone available from Emkay products at, e.g., www.emkayproducts.com. It can be appreciated that other microphones or transducers are suitable for use in the device and methods set forth herein including e.g., the Parker Aquaflex Ultrasound Gel Pad from Parker Laboratories at, e.g., www.parkerlabs.com.

The presently preferred microphone, however, is the Hydrophone DolphinEAR microphone which is available from DolphinEAR, United Kingdom (e.g., at www.dolphinear.com). This microphone has an overall frequency response range from below about 7 Hz to above about 22,000 Hz for the spectrogram software. It can be appreciated by one of skill in the art that the response range can be attenuated as desired at either end of the spectrum particularly by choice of the encasing material if any is to be used, for example, epoxy (hard casing) will attenuate sound in the 0–50 Hz range. One advantage of the hydrophone DolphinEAR is its versatile ability for remote monitoring (DE 500), e.g., via a mobile telephone interface or VHF/UHF radio system or other telemetry devices known in the art.

Figure 1:
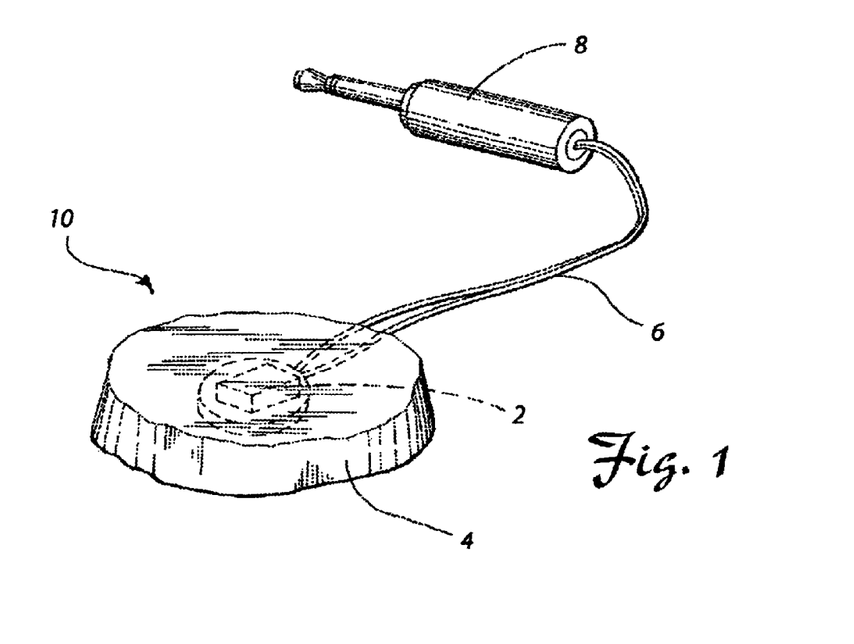
FIG. 1 is a perspective view of one embodiment of the invention showing a phantom line of the recording microphone contained within a suitable casing material.

In the embodiment shown in FIG. 1, the device 10 is comprised of a microphone or transducer 2 which is embedded in a suitable encasing material 4 such as a rubber, silicone, latex, polyurethane, plastic or other polymer, or a gel or the like. The microphone 2 is connected to a cable 6 which is in turn connected to a means for connecting the microphone 2 to a recording device (not shown). The connecting means can be a plug 8 of most any desired configuration. As shown in FIG. 1, plug 8 can be a standard BNC connector or male plug that is configured complimentary to the female receptacle of the recording device (not shown).

In one embodiment, the encasing material 4 for the microphone 2 can be a liquid latex such as is available from, e.g., www.liquid-latex.com. For example, the ingredients of the latex can comprise from about 65% water about 34.7% natural Latex sap and about 0.3% ammonia. The microphone is placed in a mold, e.g., an aluminum mold and set at a desired level therein. The liquid latex composition is then placed in the mold surrounding the microphone and allowed to cure. When cured, the ammonia and water evaporate and the latex remains.

Figure 2:
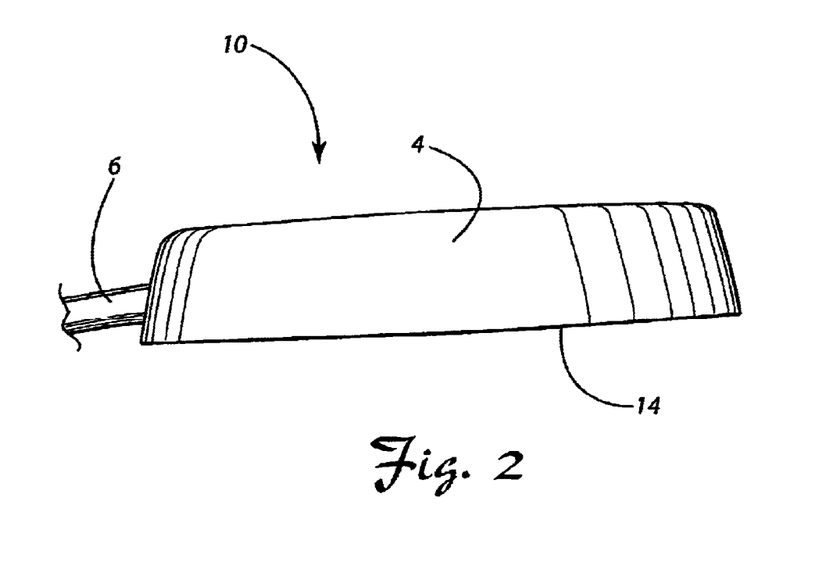
FIG. 2 is a top plan view of the recording microphone of the invention encased in a polyurethane rubber encasing material.
Figure 3:
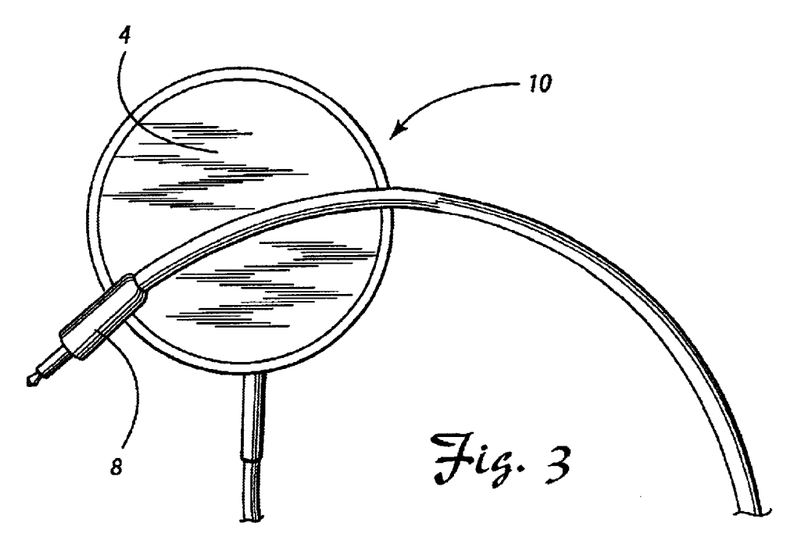
FIG. 3 is a side view of the recording microphone of the invention encased in a polyurethane rubber encasing material.
Figure 4:
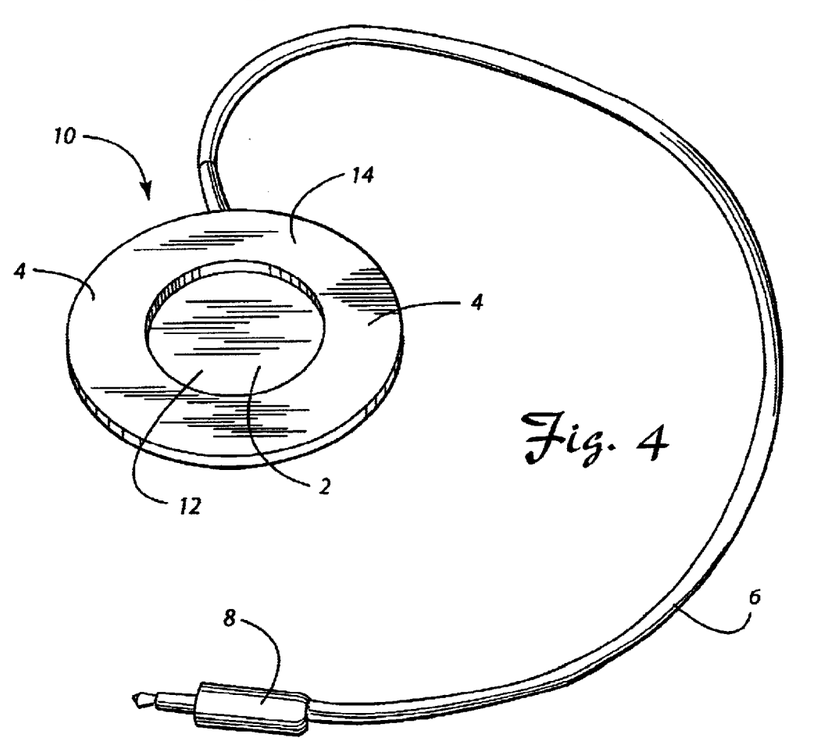
FIG. 4 is a bottom plan view of the recording microphone of the invention encased in a polyurethane rubber encasing material. The recording surface of the microphone is shown exposed within the rimmed edge of polyurethane encasing material.

In the embodiment shown in FIGS. 2–4, the microphone 2 is embedded within a casing material 4 which is a polyurethane rubber such as is available from, e.g., Smooth-On, e.g., at www.smooth-on.com. In the embodiment shown in FIG. 4, the rubber casing 4 suspends the microphone 2 such that the recording surface 12 is not enclosed within rubber casing 4. Rather rubber casing 4 forms a rimmed edge 14 around the recording surface 12 of microphone 2 creating a cavity or air space between the body of the horse (not shown) and the microphone 2 recording surface 12 when the device 10 is placed at the desired location on the horse's head. The rimmed edge 14 of the encasing material (rubber casing) 4 is held in firm contact with the horses skin. The cavity created by rimmed edge 14 can form an air space or can be filled with a desired material, e.g., ultrasound gel, for transmission of the respiratory sounds to the recording surface 12 of microphone 2.

Figure 5:
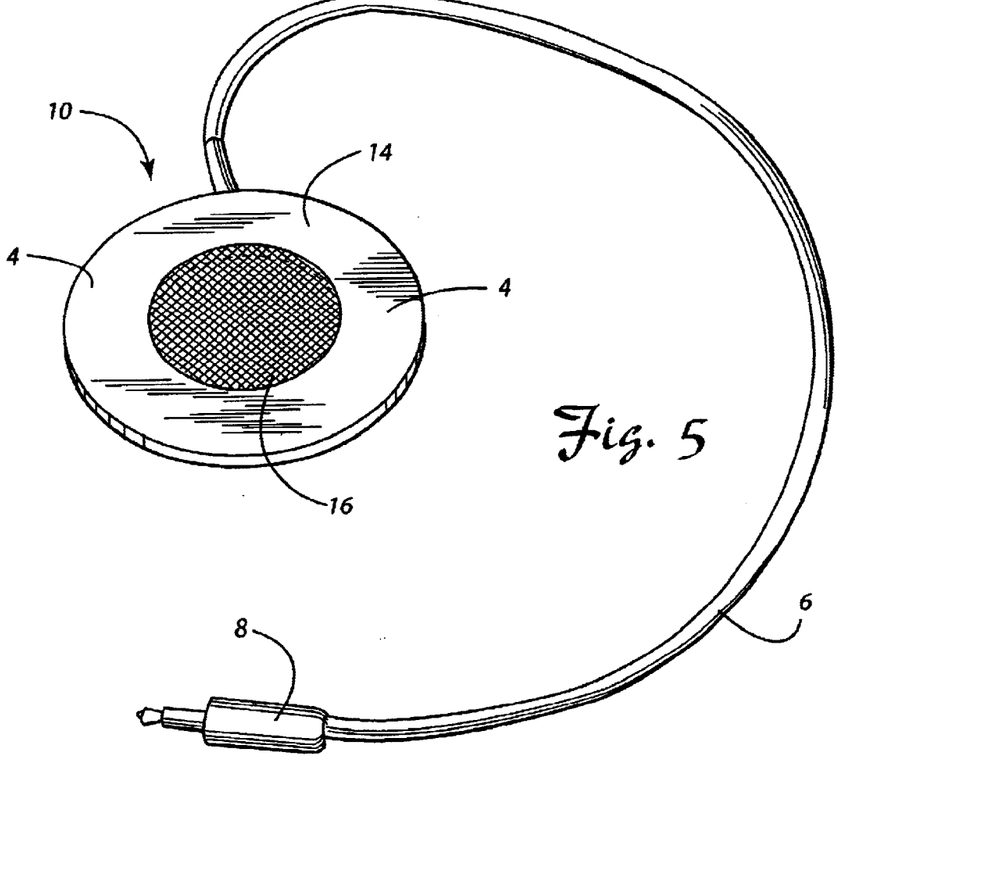
FIG. 5 is a bottom plan view of one embodiment of the invention showing the recording microphone encased in a polyurethane rubber encasing material and with a membrane covering the surface of the cavity created by the rimmed edge of the polyurethane encasing material.

In the embodiment shown in FIG. 5, the microphone (not shown) is embedded within a casing material 4 which is a polyurethane rubber such as is available from, e.g., Smooth-On, e.g., at www.smooth-on.com. In the embodiment shown in FIG. 4, the rubber casing 4 suspends the microphone such that the recording surface (not shown) is not enclosed within rubber casing 4. Rather, rubber casing 4 forms a rimmed edge 14 around the recording surface of the microphone creating a cavity or air space which is covered by membrane 16. When the device 10 is placed at the desired location on the horse's head, the rimmed edge 14 of the encasing material (rubber casing) 4 and membrane 16 are held in firm contact with the horses skin. The cavity created by rimmed edge 14 form a space with the recording surface 12 and the membrane 16. This space is preferrably filled with air or it can be filled with another desired material, e.g., ultrasound gel, for enhancement of transmission of the respiratory sounds to the recording surface of the microphone.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method for detecting an upper respiratory condition or for predicting the performance potential of a horse exercising under field conditions comprising:
    (A) placing a device comprised of at least one sound transducer at a preselected location on the head of the subject horse;
    (B) exercising the subject horse;
    (C) recording the sounds of breathing produced thereby; and
    (D) analyzing the recorded sound.

2. The method of claim 1, wherein the field condition is a race.

3. The method of claim 1, wherein the sound transducer is a microphone.

4. The method of claim 3, wherein a recording surface of the microphone is in direct contact with the horse's skin overlying the skull.

5. The method of claim 4 wherein the preselected location is directly over the frontal sinus or over the nasal turbinates of the horse.

6. The method of claim 1, wherein the preselected location is on the forehead of the horse.

7. A device for recording upper airway sounds in a horse exercising under field conditions comprising:
    (A) a transducer suitable for detection of upper airway sound;
    (B) means for attaching the transducer to the head of a horse at a preselected location; and (C) recording means for recording the detected upper airway sound.

8. The device of claim 7, wherein the transducer is a microphone.

9. The device of claim 7, wherein the preselected location is on the forehead of the horse.

10. The device of claim 7, wherein the preselected location is on the forehead of the horse and a recording surface of the transducer is in held direct contact with the skin of the horse directly overlying the skull, the frontal sinus or the nasal turbinate of the horse.

11. The device of claim 7, wherein the attaching means is a blinkers-type hood having a pouch thereon for attaching the transducer to the head of a horse at the preselected location.

12. The device of claim 7, wherein the transducer is embedded in a suitable encasing material.

13. The device of claim 12, wherein the suitable casing material is selected from the group consisting of: rubber, silicone, latex, polyurethane, plastic; a polymer and a gel.

14. The device of claim 12, wherein the suitable casing material forms a rimmed edge or shoulder around the recording surface of the transducer thereby creating a cavity between the head of the horse and a recording surface of the transducer when the device is placed at the preselected location on the horse's head.

15. The device of claim 14, further comprising a membrane covering the cavity created by the rimmed edge or shoulder.

16. The device of claim 15, wherein the cavity contains a suitable fluid.

17. The device of claim 16, wherein the suitable fluid is selected from the group consisting of a gel, air, and water.

* * * * *